United States Patent [19]

Reichel et al.

[11] Patent Number: 4,960,108

[45] Date of Patent: Oct. 2, 1990

[54] LASER-INDUCED SHOCKWAVE LITHOTRIPSY

[75] Inventors: Erich Reichel; Heinz Schmidt-Kloiber, both of Graz; Karl Groke, Eggersdorf, all of Austria

[73] Assignee: Leopold & Co. Chem. Pharm. Fabrik Gesellschaft M.B.H., Graz, Austria

[21] Appl. No.: 237,228

[22] Filed: Aug. 26, 1988

[30] Foreign Application Priority Data

Aug. 28, 1987 [DE] Fed. Rep. of Germany ....... 3728814

[51] Int. Cl.$^5$ .............................................. A61B 17/22
[52] U.S. Cl. ................................... 128/24 A; 606/127; 606/3
[58] Field of Search .................. 128/24 A, 328, 303.1, 128/395, 396, 397, 398, 399; 606/127, 128

[56] References Cited

U.S. PATENT DOCUMENTS

| | | | |
|---|---|---|---|
| 3,942,519 | 3/1976 | Shock | 128/303.1 |
| 4,469,098 | 9/1984 | Davi | 128/303.1 |
| 4,832,023 | 5/1989 | Murphy-Chutorian | 128/303.1 |

FOREIGN PATENT DOCUMENTS

| | | | |
|---|---|---|---|
| 380634 | 11/1985 | Austria . | |
| 382777 | 9/1986 | Austria . | |
| 2252665 | 5/1973 | Fed. Rep. of Germany . | |
| 3422249 | 12/1985 | Fed. Rep. of Germany . | |
| 3026868 | 3/1986 | Fed. Rep. of Germany . | |
| 3506249 | 8/1986 | Fed. Rep. of Germany | 128/328 S |
| 3517020 | 8/1986 | Fed. Rep. of Germany | 128/328 S |
| 86/06269 | 11/1986 | PCT Int'l Appl. | 128/328 S |
| 1403900 | 8/1975 | United Kingdom . | |

OTHER PUBLICATIONS

H. Schmidt-Kloiber, "Aktuelle Nephrologie" 1, 140-144 (1978).
Ell et al., "DMW 1986", 111 (31/32), p. 1217 (1986).
H. Schmidt-Kloiber & E. Reichel, "Acustica", vol. 54, 287 (1984).
H. Schmidt-Kloiber, E. Riechel et al., "Biomed.Technik" 30, 173-181 (1985).
E. Reichel, H. Schmidt-Kloiber et al., "Proceedings of the 7th Congress International Society of Laser Surgery and Medicine in Connection with Laser 87 Optoelectronics", 375-379, Springer Verlag (1988).

*Primary Examiner*—Kyle L. Howell
*Assistant Examiner*—K. M. Pfaffle
*Attorney, Agent, or Firm*—Wenderoth, Lind & Ponack

[57] ABSTRACT

Improved laser-induced shockwave lithotripsy in which pulsed laser radiation situated in the infrared region is concentrated by means of an optical wave guide at a concrement to be destroyed which is surrounded with an aqueous rinsing liquid. The concrement is destroyed mechanically by laser-induced breakdown of the rinsing liquid, giving rise to shockwave and cavitation. The improvement resides in the presence in the rinsing liquid of a metal compound selected from the group consisting of water-soluble salts of metals of the ferrous group of the periodic table, complex compounds of said metals of the ferrous group of the periodic table, water-soluble salts of magnesium and water-soluble salts of calcium, the metal compounds being present in a concentration not exceeding 50 mmol/l, relative to their metal content. The presence of the metal compounds lowers the energy required for said breakdown.

9 Claims, No Drawings

LASER-INDUCED SHOCKWAVE LITHOTRIPSY

FIELD OF THE INVENTION

The subject of the present invention is a method for laser-induced shockwave lithotripsy with which concrements located in human or animal tissue or in body cavities, such as kidney stones, ureter stones, gall stones, calcified tissue, saliva stones or the like are destroyed without impairing the surrounding tissue.

A further subject of the present invention is such a method in which the frequency of the laser-induced breakdowns in the rinsing liquid surrounding the concrement relative to the laser pulse energy presented is considerably increased in comparison with hitherto known methods of shockwave lithotripsy and consequently makes possible a substantially more effective and shorter stone destruction.

A further subject of the present invention is such a process which effects a dispersion, which is gentle on the environment, of the concrements or stones into gravel-like and/or sand-like particles which can be continuously removed without difficulty from the affected body organ by the rinsing liquid.

BACKGROUND OF THE INVENTION

In the course of investigations to find as gentle a method as possible for destroying deposits foreign to the body, such as, for example, kidney stones, gall stones, ureter stones or calcified tissue, there was no shortage of proposals and attempts to make use of light energy instead of other forms of energy, such as ultrasound and electrical energy, for this purpose. A possibility in this connection is to apply pulsed laser radiation directly to the surface of the concrement to be destroyed and consequently to destroy the latter thermally. A successful clinical trial of this method of destroying biliferous duct stones by means of flashlamp-pulsed light from a neodymium-YAG laser is reported in DMW 1986, 111, No. 31/32, page 1217. Here laser pulses having a duration of 2 ms were concentrated on the stones via a flexible 0.2 mm thick glass fiber which was supported in a special catheter, water and contrast agent being instilled at the same time. The quantity of energy required in this thermal method is high and it is hardly possible to protect the environment of the operation area against a thermal stress.

It has also already been proposed to utilize the laser light absorbed at the surface of the stone for an electroacoustic effect, which would result in a lower energy requirement. A precondition for this is to use laser light of a wavelength which has only a low capability of penetrating the material of the stone. This applies to laser light in the visible range, for instance at 350 to 550 nm, it being necessary to match the wavelength within this range to the material of the concrement.

An apparatus for carrying out this method is described in WO 86/06269 in which a laser of the so-called "dyelaser" type is used. In addition to the disadvantage of having to match the wavelength of the laser light to the chemical nature of the concrement in order to be able to carry out the method with success, this method also has the further disadvantage of using laser light in the visible range which makes strong light filters, which impede the observation of the area of operation tremendously, necessary to protect the eyes of the operating doctor.

In "Energiewandler zur Steinzerstorung in den ableitenden Harnwegen des Menschen" ("Energy transducers for stone destruction in the human urinary discharge tracts"), Aktuelle Nephrologie 1 (1978), pages 138–144, H. Schmidt-Kloiber has already proposed using for this purpose a method in which, in the immediate vicinity of the concrement, light energy is converted into mechanical energy in the form of a cavitation bubble associated with the occurrence of shockwaves, said mechanical energy being responsible for the destruction of the concrement. For this purpose, pulsed laser light is fed via a light guide into the operation region and concentrated in the vicinity of the surface, not, however, at the surface of the stone to be destroyed, so-called laser-induced breakdowns which result in shockwaves and cavitation which effect the destruction of the stone, resulting from the high electric field strength produced in this process in the liquid environment of the stone, which environment is the result of continuous rinsing with rinsing liquid. Since the dispersion of the stone is effected in this case by the mechanical energy of the shockwaves and cavitation and is not based on an absorption of the laser light by the stone, this method, which bears the name laser-induced shockwave lithotripsy, has the advantage that its success is independent of the chemical nature of the stone and it is not necessary to rely on laser radiation of a certain wavelength. Laser light in the infra-red region can therefore be used to carry out this method, and this entails great advantages. The basic physical and technical aspects of this method and its practical execution have been described by the inventors H. Schmidt-Kloiber and E. Reichel, and also by H. Schoffmann in Biomed. Technik 30 (1985), 173–181, and also by the inventor H. Schmidt-Kloiber in Aktuelle Nephrologie 1 (1978), pages 138–144, which is incorporated therein by reference. Equipment set ups for carrying out said method are described, for instance, in Austrian Patent Nos. 382,777 and 380,634.

As was disclosed by H. Schmidt-Kloiber and E. Reichel in Acustica, vol. 54 (1984), page 284, a laser-induced breakdown takes place in liquids only at high pulse energies for any laser emission. With decreasing laser pulse energy, the frequency of the breakdowns decreases until a threshold energy is reached below which virtually no breakdowns can any longer be achieved. These results are of importance since, on the one hand, the effectiveness of the method depends on a good utilization of the laser pulses delivered, but on the other hand, the intensity to be transmitted is limited by the need to use a light guide since the intensity cannot be chosen so high that laser-induced breakdowns already occur in the light guide.

As a result of the above cited paper by H. Schmidt-Kloiber and E. Reichel in Acustica, vol. 54, it is also already known that, in in-vitro tests which were carried out with water, an aqueous solution of 27 g of sorbitol and 5.4 g of mannitol per liter and a 0.9% saline solution, the threshold energy was lowest if saline solution was used and the breakdown frequency for this solution increased more quickly with increasing pulse energy than for the other two liquids tested. These results were obtained with an experimental arrangement in which the pulsed laser light was focussed via a convergent lens in a cell which contained the experimental liquid. For an in-vivo application of the method of stone destruction, however, it has to be borne in mind that the transport of light through an optical guide signifies an energy loss so that more energy has to be presented than is necessary for an adequate breakdown frequency in accordance with the in-vitro test described above. Here, however, limits are imposed since not only must the threshold intensity for a breakdown in the light guide material not be exceeded, but also the diameter of the light guide is limited to about 1 mm for reasons of usability in the body (Biomedizinische Technik 30 (1985), page 177).

Realistic tests using light guides which were carried out within the scope of experiments which result in the present invention showed that, if laser light situated in the infra-red region is used, the threshold energy of 0.9% saline solution is still too high to achieve a usable breakdown frequency. The object therefore existed of finding liquid media with which a high breakdown frequency is achieved in physiologically compatible concentrations using a light guide. Since the breakdown is associated with the development of a brightly luminous plasma (gas bubble), it can also be detected visually and the shockwave (effect) resulting therefrom can be qualitatively assessed.

Surprisingly, it was possible to find that the compounds of the ferrous metals, iron, cobalt and nickel, and of the alkaline-earth metals magnesium and calcium have a considerably lower threshold energy than for sodium chloride in aqueous solution in much lower concentrations than for the latter and that in these solutions, said compounds are capable, in a special manner, of electron generation which expresses itself in intense plasma formation which can be recognized from an intense plasma luminescence. Said plasma luminescence is not obtained at all with 0.9% saline solution under identical experimental conditions.

SUMMARY OF THE INVENTION

The subject of the present invention is a method for laser-induced shockwave lithotripsy in which, by means of pulsed laser radiation which has a wavelength situated in the infra-red region and which is fed via an optical guide to the vicinity of the concrement to be destroyed, laser-induced breakdowns are generated in the immediate vicinity of the concrement in a rinsing liquid with which the environment of the concrement is continuously rinsed during the action of the laser radiation, which breakdowns effect shockwaves and cavitation which strike the concrement and destroy it in the process, which method is improved by using aqueous solutions of substances selected from the group. consisting of water-soluble salts and complex compounds of metals of the ferrous group of the periodic system, magnesium and calcium and mixtures thereof, which are present in a concentration not exceeding 50 mmol/l relative to the metal, as the rinsing liquid.

Suitable metals of the ferrous group are cobalt, manganese and nickel in bivalent form and also bivalent as well as trivalent iron.

Since the method of stone destruction by means of laser radiation (laser lithotripsy) is independent of the chemical nature of the concrement, this method is in no way restricted to special concrements such as ureter stones, kidney stones or gall stones, but it may be made use of for the destruction of any deposits in biological materials, tissues, blood vessels or body cavities, especially as there is the advantage that a thermal stressing of the surrounding tissue is virtually ruled out. In selecting the concentration of the metal compounds or complexes, the physiological conditions at the point of application naturally have to be borne in mind in addition to the effectiveness.

If the destruction of concrements is carried out in living organisms, in particular in a human being, it is advisable to adjust the pH of the solution according to the invention to 4–8, in particularly sensitive regions even to 4.5–6.5.

It is of great importance that the concentrations, which are effective in the context of the present invention, of the substances contained in the solution according to the invention are far below the concentration of the hitherto recommended 0.9% saline solution, which in fact corresponds to 0.15 mol/l. As a result of these very low active concentrations, much more readily physiologically compatible solutions can be prepared. The active concentrations of the individual metal salts and metal compounds according to the invention vary, but as a rule, they are between 0.015 and 50 mmol/l. It also emerged that each of the solutions according to the invention has a minimum in the threshold energy depending on the concentration. Such a phenomenon was also detected in aqueous saline solutions (Schmidt-Kloiber and Reichel, Acustica 54 (1984), page 287), but in this case the minimum was not in the region of a concentration of a few millimoles or even of fractions of millimoles per liter, but was about 0.5 to 1 mol/l, a concentration range which can no longer be utilized at all for physiological reasons.

Surprisingly, it also emerged that changing the concentration not only necessitates higher threshold field strengths, but also alters the size of the fragments produced. This may be of advantage in various applications since, depending on choice of the active compound and/or the concentration thereof in the solution, either coarse fragments are produced or else the concrements are broken down into gravel-like or pulverulent particles. In principle, it should be stated in this connection that the size of the fragments and the destruction time correlate with each other. Both the choice of the active compound and also the concentration thereof within the limits according to the invention will therefore depend on the application, depending on whether destruction in as short a time as possible or else destruction to as fine particles as possible is desired or a middle road has to be taken. The optimum composition in each case can be determined by a few tests. In general, it is true, however, that lower concentrations of the metal compounds or complexes favor the dispersion of the concrements to form pulverulent or gravel-like particles, whereas the tendency for dispersion of the concrement into coarser particles grows with increasing concentration.

As already mentioned, the optimum concentrations of the metal compounds to be chosen according to the invention are situated in various concentration ranges. Solutions which contain compounds of calcium or magnesium as active agent and in which these two metals are expediently present as soluble salts, for instance as chlorides, are preferably used in a concentration of 1 to 50 mmol/l. In this case magnesium is preferred since, despite having about the same threshold energy as calcium, it effects a better plasma formation and this can be recognized from a continuous plasma luminescence. As a consequence, more mechanical energy is liberated if magnesium compounds are used in the rinsing solution than if calcium compounds are used in the same concentration. Salts of cobalt, nickel and bivalent iron are preferably used in a concentration range of 1 to 5 mmol/l it being necessary to bear in mind the physiological compatibility at the point of application in choosing the concentration within the preferred range in the case of cobalt and nickel. The compounds of these ions also fail to reach the magnesium compounds in the intensity of the plasma formation, despite the favorable position of the threshold energy, but do, however, also offer advantages over 0.9% common salt solution in this connection.

A special position is occupied, surprisingly, by the compounds of trivalent iron which far exceed the other metal compounds to be chosen according to the invention, even those of bivalent iron, both in the position of the threshold energy and also in the intensity of the plasma formation.

Some salts or complex compounds exhibit an optimum action even at concentrations which are far below the active concentrations of the other metal compounds to be chosen according to the invention. Thus, for instance, an aqueous solution which contained only 0.05 mmol/l of trivalent iron in the form of an iron-dextran complex exhibited a threshold energy which was only about 1/5 of that of 0.9% saline solution, the intensity of the plasma luminescence exceeding that of solutions of all the other metal compounds If the same Fe(III) complex is chosen in a concentration of 0.5 mmol/l, the threshold energy is so low that it can no longer be determined with the chosen arrangement.

Trivalent iron may also be contained in the solution according to the invention as a simple salt, for example as iron trichloride. For reasons relating to simple handling and to the shelf life of the solutions, it is, however, advisable to use the trivalent iron in the form of one of its complexes. For this purpose, use may be made of any complex which contains the trivalent iron bound only tightly enough that Fe(III) ions are still released into the solution. Particularly preferred are the iron citrate complex, whose preferred concentration is in the range from 1 to 5 mmol/l, the iron tartrate complex, whose preferred concentration is 0.015 to 1 mmol/l, and the iron-dextran complexes, for instance those with an iron content of 10 to more than 30%, a molecular mass of the dextran of 2000-6000 and a proportion of dextran of up to 50%. The optimum concentration to be chosen is, in the latter case, also in the range from 0.015 to 1 mmol/l relative to the iron content. Such iron-dextran complexes are described, for example, in DE-B-3,026,868 and DE-A-3,422,249. Iron-containing complexes, such as iron-dextrins or iron sucrate, which are common in pharmaceutical practice, have also proved to be suitable. These are also preferably used in a concentration of 0.015 to 1 mmol of iron per liter.

Since trivalent iron develops its activity in the context of the present invention even at extremely low concentrations, it is also possible to produce salts thereof in aqueous solution in situ by dissolving elementary iron, for example in the form of powder or as strips, the initial concentration of Fe(III) salts being increasingly raised by the action of the laser radiation.

When the solution according to the invention is used in laser lithotripsy, it is frequently advisable for physiological reasons for the osmolarity of said solutions to be roughly in the region of a physiological saline solution. Since the active concentration ranges of the solutions according to the invention are much too low to be isotonic, it is advantageous to adjust the osmolarity by adding substances which are physiologically harmless and do not react in any way with the active metal compounds. For example, carbohydrates, in particular sorbitol or mannitol or mixtures of the same, or even common salt may be used as such substances, common salt being preferably used to adjust the osmolarity. As investigations have shown, these additives have virtually no effect on the threshold energy of the solutions and the plasma formation.

The preparation of the solutions according to the invention is accomplished in the usual manner by dissolving the metal salts or complexes in water or alternatively in a solution of physiologically compatible, inert substances whose concentration should be so chosen that they produce an approximately isotonic solution together with the active constituents. Subsequently, the pH is adjusted, if necessary, and the solution is sterilized, for which purpose, depending on the stability of the active substance, both a heat sterilization and a sterile filtration are suitable. It is also possible to mix the solution according to the invention together only immediately before use. For this purpose, a suitable quantity of a concentrated salt solution or of a concentrated solution of a complex is provided in sterile form, for example in an ampule, which is then added immediately before use to the desired quantity of sterile water or to a solution of suitable osmolarity and uniformly dispersed therein. However, the metal salt or the complex compound can also be provided in solid form, for example as a lyophilisate, which is then taken up in a small quantity of sterile water immediately before use. The solution thus resulting is then made up to the final volume. The procedure of preparation on the spot suggests itself especially in those cases where the chosen salt or the complex compound is unstable in aqueous solution and does not withstand, for instance, in dilute solution a heat treatment such as is necessary for sterilization. Preparation on the spot can, however, also be beneficial in cases where water ad injections or physiological saline solution are available for all possible purposes and the storage of the solution according to the invention in ready-to-use form is not desirable for space reasons, or transportation over long distances is necessary. This procedure is advisable especially in those cases where salts or complexes of trivalent iron are to be used as active agent since dilute solutions of trivalent iron entail problems with shelf life and, in addition, iron (III) compounds are used in such a low concentration that, even when isotonic solutions are desirable, physiological saline solution which is available in every hospital and which then does not require any adjustment in concentration before mixing, can be used as the base solution.

The solution according to the invention can be used as rinsing solution in all the versions of laser-induced shockwave lithotripsy, regardless of the method in which the radiation is concentrated in the area of operation. As a result of using laser light in the infra-red region, if the necessary eye protection is used, the visual perception by the doctor is not restricted, and this is of particular importance for carrying out such a difficult method which time and again makes a correct adjustment of the position of the end of the catheter necessary. Furthermore, laser systems which employ infra-red have been known for years to be extremely reliable and simple to operate. This applies particularly to neodymium-YAG lasers. In relation to the low threshold energy of these solutions, in particular when solutions containing trivalent iron as active agent are involved, they can also be used in cases where a particularly strong focusing of the laser beams used has to be rejected for physiological or equipment reasons, or longer laser pulses than those hitherto described have to be used for other reasons.

In the examples below, a few particularly well-tried formulations for solutions according to the invention are specified. Furthermore, measurements which were obtained with the solutions according to the invention are specified.

Since the threshold energy is dependent on the nature and the wavelength of the laser beam and geometrical data of the laser beam also enter into the measurements, numerical values which were obtained with different set ups cannot be compared with each other. Therefore, comparison with 0.9% saline solution which was included in every experimental series as a standard, was chosen as the objective assessment criterion. The threshold energy of 0.9% saline solution is set at 100% and that of the experimental solution is specified in per cent relative to the 0.9% common salt solution. The energy of the laser radiation which was used for the measurements was chosen as that which was just sufficient, in the case of 0.9% common salt solution, to achieve a breakdown, frequency of 80–100%.

A further assessment was provided by experiments in which, for transporting the light of the laser beam, use was made of a light guide which terminates in a cell which is filled with the experimental liquid. A t the input side, the light guide was exposed to the pulsed light from a Q-switched neodymium-YAG laser having an energy of 39 mJ. The pulse repetition frequency was 50 hertz. The energy of the laser radiation at the output side was 36 mJ. As a criterion for the action of the experimental liquid, on the one hand, the occurrence or the intensity of the plasma luminescence was assessed visually and, on the other hand, loosely mixed stone material was introduced into the cell in the vicinity of the output side of the light guide and the dispersion was assessed, again visually. Some of the results of such experiments are given in the table in Example 9 and also in Example 10.

EXAMPLE 1

50 mmol of magnesium chloride are dissolved in a little less than 1 liter of a solution which contains 80 mmol of common salt dissolved in water. After solution and making up to a volume of 1 liter has taken place, an isotonic solution is obtained which is sterilized by heat sterilization at 110° C. It can be used with good success to destroy ureter stones.

EXAMPLE 2

50 mmol of calcium chloride are dissolved in 800 ml of an aqueous solution of 80 mmol of common salt, whereafter adjustment to 1 liter is made with water ad injectionem. After heat sterilization, the solution is suitable for destroying ureter stones.

EXAMPLE 3

1 mmol of Fe(III) citrate is dissolved in 900 ml of an aqueous solution of 154 mmol of Nacl. After adjusting the pH to pH 4.5 with sodium hydroxide solution, the solution is made up to 1 liter. It is sterilized for 30 minutes at 112° C.

This solution is physiologically outstandingly compatible and is suitable both for use in a ureter probe and also in a probe which is introduced into the body by punctuating.

EXAMPLE 4

As described in Example 3, a solution is prepared which contains 1 mmol of Fe(III)/l, but as the tartrate. It can also be used like the solution according to Example 3.

EXAMPLE 5

As described in Example 3, a solution is prepared with an Fe(III) content of 0.02 mmol/l, an iron (III)-dextran complex having an iron content of 16.0% in which the dextran had a proportion of 15–25% being used as active substance. The solution is sterilized for 60 minutes at 113° C. Despite the lower concentration than that according to Example 3, it can be used in precisely the same way as that solution.

EXAMPLE 6

Enough of the Fe(III)-dextran complex as is used in Example 5 is dissolved in the isotonic solution of a mixture of 27 g of sorbitol and 5.4 g of xylitol per liter for the solution to contain 0.02 mmol of Fe(III) per liter. It is sterile-filtered and can be used in precisely the same way as the solution according to Example 5.

EXAMPLE 7

An aqueous solution having an Fe(III) content of 20 mmol/l is prepared from the same iron-dextran complex as in Example 5. This solution is filled into 5 ml ampules and heat-sterilized. Before being used as rinsing solution, the contents of an ampule are uniformly distributed in 4.5 l of 0.9% saline solution.

EXAMPLE 8

1 mmol of $CoCl_2$ is dissolved in a little less than 1 liter of a solution of 154 mmol of NaCl and further treated as described in Example 3. It can be used as rinsing solution in destroying bladder stones.

EXAMPLE 9

For various solutions according to the invention, their properties compared with 0.9% NaCl solution were determined, the work being carried out as described previously, without and with light transport through a light guide. The procedure for determining the threshold energy was as follows: laser pulses having a wavelength of 1064 nm and a duration of 8 ns were focussed by means of a convergent lens. A cell was fitted insertably in such a manner that the focal point occurs in the interior space. The cell was filled with 0.9% saline solution and the laser energy was so adjusted that, with this saline solution, breakthroughs just occurred with a frequency of 80–100%. Then the variation of the laser pulse with time is recorded, without a cell and subsequently with a cell inserted which contains the respective experimental liquid. A breakdown can be detected from the fact that the laser light passing through is suddenly cut off. The earlier this cut off occurs, the lower is the threshold energy. The numerical value of the threshold energy is calculated from the area of the original laser pulse up to the cut off point. The threshold energies obtained in mJ are specified in the table below. The energy of the laser pulse in this experimental series was 6.2 mJ upstream of the cell, and the energy at the focal point was 3.8 mJ. Furthermore, the threshold energy was calculated in per cent relative to NaCl=100% for each experimental solution. For the experiments in which the light first passes through a light guide with a diameter of 0.6 mm, the energy at the output end of the fiber was 36 mJ with a pulse repetition rate of 50 Hz. The following assessment scale was used for the optical evaluation of the plasma luminescence:

0: No visually detectable breakdown
1: Sporadic occurrence of breakdowns can be detected from flashing plasma luminescence
2: "Continuous" occurrence of plasma luminescence
3: Strong, "continuous" occurrence of spatially extended plasma luminescence The wavelengths and pulse duration of the laser light used were the same as in the experiments without an optical light guide.

As test solutions, use was made of those of the active compounds in double-distilled water as solvent, and also of those which were rendered isotonic by adding NaCl. The results are summarized in the table below.

TABLE

| Experiment No. | Compound | Conc mmol/l (metal) | LM | ES mJ | ES/$E_{NaCl}$ % | LIB |
|---|---|---|---|---|---|---|
| Standard | NaCl 0.9% | | | 1.52 | 100 | 0 |
| 1 | FeCl$_3$ | 0.2 | H$_2$O | 0.10 | 6.58 | — |
| 2 | FeCl$_3$ | 0.1 | H$_2$O | 0.10 | 6.58 | — |
| 3 | FeCl$_3$ | 0.04 | H$_2$O | 0.10 | 6.58 | — |
| 4 | FeCl$_3$ | 0.2 | NaCl | 0.10 | 6.58 | — |
| 5 | FeCl$_3$ | 0.1 | NaCl | 0.10 | 6.58 | — |
| 6 | FeCl$_3$ | 0.04 | NaCl | 0.10 | 6.58 | — |
| 7 | Fe citrate | 5 | NaCl | 0.51 | 33.56 | 3 |
| 8 | Fe citrate | 1 | NaCl | 0.47 | 30.92 | 1 |
| 9 | Fe tartrate | 0.9 | NaCl | 0.59 | 38.82 | 3 |
| 10 | Fe tartrate | 0.1 | NaCl | 0.61 | 40.13 | 2.5 |
| 11 | Fe-dextran | 0.9 | NaCl | 0.0 | 0 | 3 |
| 12 | Fe-dextran | 0.5 | NaCl | 0.0 | 0 | 3 |
| 13 | Fe-dextran | 0.02 | NaCl | 0.37 | 24.35 | 3 |
| 14 | CoCl$_2$ | 5 | NaCl | 0.97 | 63.82 | 2 |
| 15 | CoCl$_2$ | 1 | NaCl | 0.60 | 39.48 | — |
| 16 | NiCl$_2$ | 1 | NaCl | 0.96 | 63.17 | 1 |
| 17 | MgCl$_2$ | 50 | NaCl | 1.17 | 76.99 | 2 |
| 18 | MgCl$_2$ | 1 | NaCl | 0.52 | 34.22 | 1 |
| 19 | CaCl$_2$ | 50 | NaCl | 1.14 | 75.01 | 1 |
| 20 | CaCl$_2$ | 1 | NaCl | 0.78 | 51.32 | — |

Legend:
LM = Solvent
H$_2$O = Double-distilled water
NaCl = Solution rendered isotonic with NaCl
ES = Threshold energy of the individual solutions
$E_{NaCl}$ = Threshold energy of a 0.9% NaCl solution
LIB = Assessment rating for the plasma luminescence Surprisingly, as the table reveals, the values for the threshold energy and the intensity of the plasma formation are not completely in agreement, which reveals that yet other criteria in addition to the level of the threshold energy are also apparently involved in the achievement of the action according to the invention.

EXAMPLE 10

In a further test arrangement, the laser light was passed through a light guide into a cell which was filled with solutions of an iron-dextran complex having a concentration of 0.1 mmol/l, solution 1 containing the iron complex in dissolved double-distilled water, solution 2 containing it dissolved in 0.9% saline solution and solution 3 containing it dissolved in a solution of 27 g of sorbitol and 5.4 g of mannitol per liter.

A uric acid stone was loosely fixed in the cell. The stone was broken down to form gravel-like material by the laser pulses presented which had the same energy as in Example 9 in the experiments using a light guide. No difference in the effectiveness of the stone destruction was observable between the three solutions.

The following procedure is preferably adopted for the clinical application of the method according to the invention for laser-induced shockwave lithotripsy to the destruction of stones (calculi) which are situated in the interior of the human body:

An endoscope is inserted either through tracts in the body of the patient, such as, for example through the ureter in the destruction of ureter stones, or alternatively percutaneously, until the vicinity of the stone to be destroyed is reached. A light guide is pushed forward through this catheter, which has an inside diameter of, for example, 2 mm, into the vicinity of the stone so that the concrement to be destroyed is situated in front of the light guide. An image guide which makes it possible to observe the area of operation and makes possible a removal of the rinsing liquid which is continuously pumped through the cavities of the three conductors to the area of operation is likewise inserted. Such an apparatus is described, for example, by H. Schmidt-Kloiber in Aktuelle Nephrologie 1 (1978), page 143. The rinsing liquid which has the composition according to the present invention must fill the area of operation completely. The laser equipment used is preferably a neodymium-YAG laser which generates laser light of a wavelength of 1064 nm. The pulse duration of the laser light is, for example, $1.5 \times 10^{-8}$ sec, the pulse repetition frequency is 50 hertz, and, with a light guide core cross-section of 600 µm, the energy of the laser beam at the output point should not be less than 25 mJ. These laser pulses are focussed in the space between the end of the optical guide and the stone to be destroyed in a manner such that laser-induced breakdowns whose shockwaves must strike the surface of the stone take place at this point. With a suitably rapid sequence of breakdowns which can be achieved by the choice of the rinsing liquid according to the invention and an energy of the laser pulses which are able to pass through the optical guide without destroying the same, the stone is preferably dispersed to form particles with a size of about 1 mm which are continuously discharged with the rinsing liquid. This operation is continued until the stone is completely dissolved, which is possible within a few minutes under optimum conditions for ureter stones of the oxalate stone type.

What we claim is:

1. In a method for laser-induced shockwave lithotripsy comprising:
   a. surrounding a concrement to be destroyed with an aqueous solution and
   b. feeding pulsed laser radiation of a wave length situated on the infrared region via an optical wave guide to the immediate vicinity of the concrement, whereby said laser radiation in a vicinity of the surface of the concrement is concentrated, thereby generating in said aqueous solution laser-induced breakdowns, said breakdowns effecting shockwaves and cavitation in said aqueous solution in the immediate vicinity of said concrement, and thereby destroying the concrement with said shockwaves while the concrement is continuously rinsed with the aqueous solution during said pulsed laser radiation,
   wherein the improvement comprises said aqueous solution containing at least one metal compound selected from the group consisting of water-soluble salts of metals of the ferrous group of the periodic table, complex compounds of said metals of the ferrous group of the periodic table, water-soluble salts of magnesium and water soluble salts of calcium, said metal compound being present in a concentration not exceeding 50 mmol/l, based on its metal content.

2. The method as claimed in claim 1, wherein the aqueous solution additionally contains at least one physiologically compatible additive which is inert to said metal compound, in an amount necessary to alter the osmolarity of said aqueous solution to a level which corresponds substantially to that of a physiologically saline solution.

3. The method as claimed in claim 2, wherein the physiologically compatible additive is common salt.

4. The method as claimed in claim 3, wherein the aqueous solution has a pH in the range of 4 to 8.

5. The method as claimed in claim 3, wherein the metal-compound dissolved in the aqueous solution is a complex compound of trivalent iron.

6. The method as claimed in claim 1, wherein the metal-compound dissolved in the aqueous solution is a complex compound of trivalent iron with citrate, which is present in a concentration of 1 to 5 mmol/l based on the iron content of said complex compounds.

7. The method as claimed in claim 1, wherein the metal compound dissolved in the aqueous solution is a complex compound of trivalent iron with tartrate, which is present in a concentration of 0.015 to 1 mmol/l based on the iron content of said complex compounds.

8. The method as claimed in claim 1, wherein the metal compound dissolved in the aqueous solution is an iron (III)-dextran complex, which is present in a concentration of 0.015 to 1 mmol/l based on the iron content of said dextran complex.

9. The method as claimed in claim 1, wherein the metal compound dissolved in the aqueous solution is a soluble salt of magnesium, which is present in a concentration of 1 to 50 mmol/l.

* * * * *